United States Patent
Zhou et al.

(10) Patent No.: US 10,970,436 B2
(45) Date of Patent: Apr. 6, 2021

(54) METHOD FOR NUMERICALLY SIMULATING ORTHODONTIC EFFECT OF ORTHODONTIC APPLIANCE

(71) Applicant: WUXI EA MEDICAL INSTRUMENTS TECHNOLOGIES LIMITED, Wuxi (CN)

(72) Inventors: Ketuo Zhou, Wuxi (CN); Lei Huang, Wuxi (CN)

(73) Assignee: WUXI EA MEDICAL INSTRUMENTS TECHNOLOGIES LIMITED, Wuxi (CN)

(*) Notice: Subject to any disclaimer, the term of this patent is extended or adjusted under 35 U.S.C. 154(b) by 337 days.

(21) Appl. No.: 15/846,225

(22) Filed: Dec. 19, 2017

(65) Prior Publication Data
US 2018/0189434 A1 Jul. 5, 2018

(30) Foreign Application Priority Data
Dec. 30, 2016 (CN) .......................... 201611259482.8

(51) Int. Cl.
*G06F 30/23* (2020.01)
*G06T 17/20* (2006.01)
(Continued)

(52) U.S. Cl.
CPC ............ *G06F 30/23* (2020.01); *A61C 7/002* (2013.01); *G06T 17/20* (2013.01); *G16H 30/40* (2018.01); *G16H 50/50* (2018.01)

(58) Field of Classification Search
CPC ........ G06F 30/23; G16H 50/50; G16H 30/40; A61C 7/002; G06T 17/20
(Continued)

(56) References Cited

U.S. PATENT DOCUMENTS 5,431,562 A * 7/1995 Andreiko ................. A61C 7/00
433/24
5,602,891 A * 2/1997 Pearlman ............... A61B 6/463
250/363.01
(Continued)

OTHER PUBLICATIONS

Hiromi Ryokawa et. al., The mechanical properties of dental thermoplastic materials in a simulated intraoral environment, Orthodontic Waves 65 (2006) 64-72. (Year: 2006).*

*Primary Examiner* — Justin C Mikowski
(74) *Attorney, Agent, or Firm* — Jun He Law Offices P.C.; James J. Zhu (57) ABSTRACT

The present application discloses a method for numerically simulating orthodontic effect of an orthodontic appliance. The method comprising: providing a numerical dental model representing a patient's dental tissues, wherein the numerical dental model comprises mechanical parameters and geometrical parameters of the patient's dental tissues; providing a numerical orthodontic appliance model representing an orthodontic appliance, the orthodontic appliance corresponding to an expected orthodontic state, and the numerical orthodontic appliance model comprising mechanical parameters and geometrical parameters of the orthodontic appliance; combining the numerical orthodontic appliance model with the numerical dental model to simulate wearing of the orthodontic appliance on the patient's dental tissues; calculating orthodontic change after the wearing of the orthodontic appliance on the patient's dental tissues, based on the mechanical parameters and geometrical parameters included in the numerical orthodontic appliance model and the numerical dental model respectively; and assessing the orthodontic effect of the numerical orthodontic appliance model based on the orthodontic change.

15 Claims, 7 Drawing Sheets

(51) Int. Cl.
*G16H 50/50* (2018.01)
*A61C 7/00* (2006.01)
*G16H 30/40* (2018.01)

(58) Field of Classification Search
USPC .......................................................... 703/2
See application file for complete search history.

(56) References Cited

U.S. PATENT DOCUMENTS

| | | | | |
|---|---|---|---|---|
| 5,975,893 | A * | 11/1999 | Chishti | B33Y 80/00 |
| 6,217,334 | B1 * | 4/2001 | Hultgren | A61C 9/0006 |
| | | | | 433/215 |
| 6,227,850 | B1 * | 5/2001 | Chishti | A61C 7/00 |
| | | | | 433/24 |
| 6,744,914 | B1 * | 6/2004 | Rubbert | A61C 7/146 |
| | | | | 382/154 |
| 8,359,114 | B2 * | 1/2013 | Steingart | A61C 1/082 |
| | | | | 700/98 |
| 9,642,685 | B2 * | 5/2017 | Brodkin | A61C 13/0004 |
| 9,937,023 | B2 * | 4/2018 | Andersson | A61C 9/0006 |
| 10,478,269 | B2 * | 11/2019 | Jin | A61C 7/002 |
| 2002/0015934 | A1 * | 2/2002 | Rubbert | B33Y 50/00 |
| | | | | 433/29 |
| 2007/0087302 | A1 * | 4/2007 | Reising | A61C 7/145 |
| | | | | 433/24 |
| 2013/0041630 | A1 * | 2/2013 | Gilles | A61C 13/0004 |
| | | | | 703/1 |
| 2016/0098499 | A1 * | 4/2016 | Heirman | G06F 30/20 |
| | | | | 703/2 |

* cited by examiner

Fig. 8

METHOD FOR NUMERICALLY SIMULATING ORTHODONTIC EFFECT OF ORTHODONTIC APPLIANCE

CROSS REFERENCE TO RELATED APPLICATION

The present application claims priority and benefit to Chinese Patent Application No. 201611259482.8 filed on Dec. 30, 2016, the content of which is incorporated hereinto by reference.

TECHNICAL FIELD

The present disclosure relates to the field of orthodontics, and more particularly, to a method for numerically simulating orthodontic effect of a series of orthodontic appliances.

BACKGROUND

In order to achieve orthodontic treatment for a patient's teeth, a variety of orthodontic devices have been developed at present. Compared with the traditional orthodontic technology using fixed brackets, a new technology of invisible orthodontic treatment uses a series of invisible appliances (also known as shell appliances), rather than using brackets and wires. This type of invisible orthodontic appliance is made of a high-performance, resilient polymer material that satisfies requirements on biocompatibility, which makes the orthodontic process almost unobservable by others and thus not influence daily life and social activities. In addition, since a patient can put on and remove the appliance by himself, his or her oral hygiene can be normally maintained, and the whole orthodontic process would not cost much time and efforts.

In the existing methods of designing and manufacturing appliance, design of the teeth arrangement plays a very important role. With the rapid development of computer technology, teeth arrangement design in a three-dimensional environment of a virtual teeth orthodontic system is gradually substituting the traditional manual teeth arrangement process. However, no matter it is a manual teeth arrangement or an automatically numerical teeth arrangement, the currently available teeth arrangement designs are based on experience of clinical staffs, and they still stay at the stage of geometric design. Therefore, a doctor or designer cannot effectively understand and evaluate the orthodontic effect of the orthodontic appliance when designing teeth arrangement.

SUMMARY

The existing methods of designing an orthodontic appliance are not convenient to a doctor or an orthodontic designer to learn the orthodontic effects of the orthodontic appliance, which limits the flexibility and reliability of the orthodontic appliance design significantly. In particular, the current teeth arrangement design is still at a stage of geometric design and lacks of the analysis of dynamic force state of teeth during the process of orthodontic treatment. Especially, the current teeth arrangement design lacks of a means for verifying the teeth movement under a dynamic force.

The inventors of the present application found that, the above-mentioned drawbacks of the conventional methods of designing an orthodontic appliance may result in a number of problems, which are set forth as follows.

1. Due to the insufficient connection between clinical medicine and biomechanics, the mechanical guidance for teeth load is deficient in the process of teeth arrangement design, which leads to the fact that the actual movement location after one step of the orthodontic treatment generally does not fully coincide with the designed movement location set in teeth arrangement design. In the design phase, there is no method of identifying and verifying the displacement deviation between the actual location and the designed location. At present, during the whole process of a teeth arrangement design, the designed displacement of the previous step is generally used as the input parameter of the subsequent step of the teeth arrangement design, which will cause the deviation between the designed displacement and the real displacement as generated in each orthodontic step to accumulate gradually. When the accumulation of deviation reaches to a certain level, the expression of the orthodontic ability of an invisible orthodontic appliance will be affected seriously.

2. Due to the insufficient connection between clinical medicine and material mechanics, the mechanical properties of an orthodontic appliance are not considered when designing the teeth arrangement. As a result, there is no force verification for an invisible orthodontic appliance in one step of the orthodontic designing process. The current teeth arrangement designing method cannot completely avoid risks, such as the orthodontic force being too large, or the force design being impossible.

3. Due to the insufficient connection between clinical medicine and manufacturing process, the constraint of thermoforming process is not considered when designing the teeth arrangement. As a result, the final geometry of an orthodontic appliance may have discrepancy with the geometry of the design expectation, thereby affecting the orthodontic effect. Currently, the geometry of an orthodontic appliance after processing cannot be predicted accurately in the design phase, and thus effective design compensation cannot be made for the discrepancy.

In order to solve at least some of the above drawbacks existing in the prior art, the inventors of the present application have proposed a method of calculating and verifying orthodontic effect of an orthodontic appliance using computer simulation technique. The method can apply a finite element simulation to the orthodontic effect of the orthodontic appliance in an early stage of the design and determine the effect of the orthodontic appliance on the teeth movement location at each teeth arrangement stage. In this way, the doctor or designer can adjust the design of the appliance based on the results of the simulation and verification, so as to achieve an optimum design for the orthodontic appliance.

In one aspect of the present application, a method for numerically simulating orthodontic effect of an orthodontic appliance is provided. The method comprising: providing a numerical dental model representing a patient's dental tissues, wherein the numerical dental model comprises mechanical parameters and geometrical parameters of the patient's dental tissues; providing a numerical orthodontic appliance model representing an orthodontic appliance, the orthodontic appliance corresponding to an expected orthodontic state, and the numerical orthodontic appliance model comprising mechanical parameters and geometrical parameters of the orthodontic appliance; combining the numerical orthodontic appliance model with the numerical dental model to simulate wearing of the orthodontic appliance on the patient's dental tissues; calculating orthodontic change after the wearing of the orthodontic appliance on the patient's dental tissues, based on the mechanical parameters and geometrical parameters respectively included in the numerical orthodontic appliance model and the numerical dental model; and assessing the orthodontic effect of the numerical orthodontic appliance model based on the orthodontic change.

It can be seen that, by applying the simulating method of the present application, a doctor or designer is able to verify the teeth displacement results for each treatment stage of the teeth movement, and in some cases, the true movement amount (instead of the designed movement amount) of the dental model can be used as the initial design model for the next orthodontic stage, which greatly improves the orthodontic effect of the orthodontic appliance. Specifically, 1. The method of the present application effectively connects a number of subject-fields through the finite element method, and provides a solution for dynamic displacement verification. In addition, the method provides true teeth displacement input for the orthodontic treatment plan, and avoids negative impact on orthodontic capacity of an orthodontic appliance as brought by accumulated design deviation.

2. The method of the present application can be used as a step of design, which can be applied to a full set of practical commercial work process including orthodontic design, manufacturing process, and clinical application. The ability of orthodontic treatment plan can be improved without increasing the costs for equipment or markedly increasing design time.

3. Due to the integration of biomechanics, material mechanics, and manufacturing process, a most suitable orthodontic appliance material and manufacturing method can be determined to match a patient's dental tissues according to the simulation results, thereby further improving the orthodontic performance applied by the invisible orthodontic appliance.

The foregoing is an overview of the present application, and details may be simplified, generalized, and omitted. Thus, those skilled in the art will recognize that this section is merely illustrative and not intended to limit the scope of the present application in any way. This overview section is neither intended to identify key features or essential features of the claimed subject matter or serve as an auxiliary means for determining the scope of the claimed subject matter.

BRIEF DESCRIPTION OF THE DRAWINGS

The foregoing and other features of the present application will be further illustrated in conjunction with the accompanying drawings and its detailed description. It should be understood that these drawings only show a few exemplary embodiments in accordance with the present application and should therefore not be construed as limitation to the scope of the present application. Unless otherwise specified, the drawings are not necessarily to scale, and similar reference numerals refer to similar parts.

DETAILED DESCRIPTION

The following detailed description refers to the accompanying drawings which is a part of this specification. The illustrative embodiments mentioned in the specification and the drawings are for illustrative purposes only and are not intended to limit the scope of the present application. It should be understood by those skilled in the art that many other embodiments may be applied and various changes may be made to the described embodiments without departing from the spirit and scope of the present application. It should be understood that the various aspects of the present application described and illustrated herein may be arranged, replaced, combined, separated and designed in accordance with a number of different configurations, all of which are incorporated herein.

Figure 1:
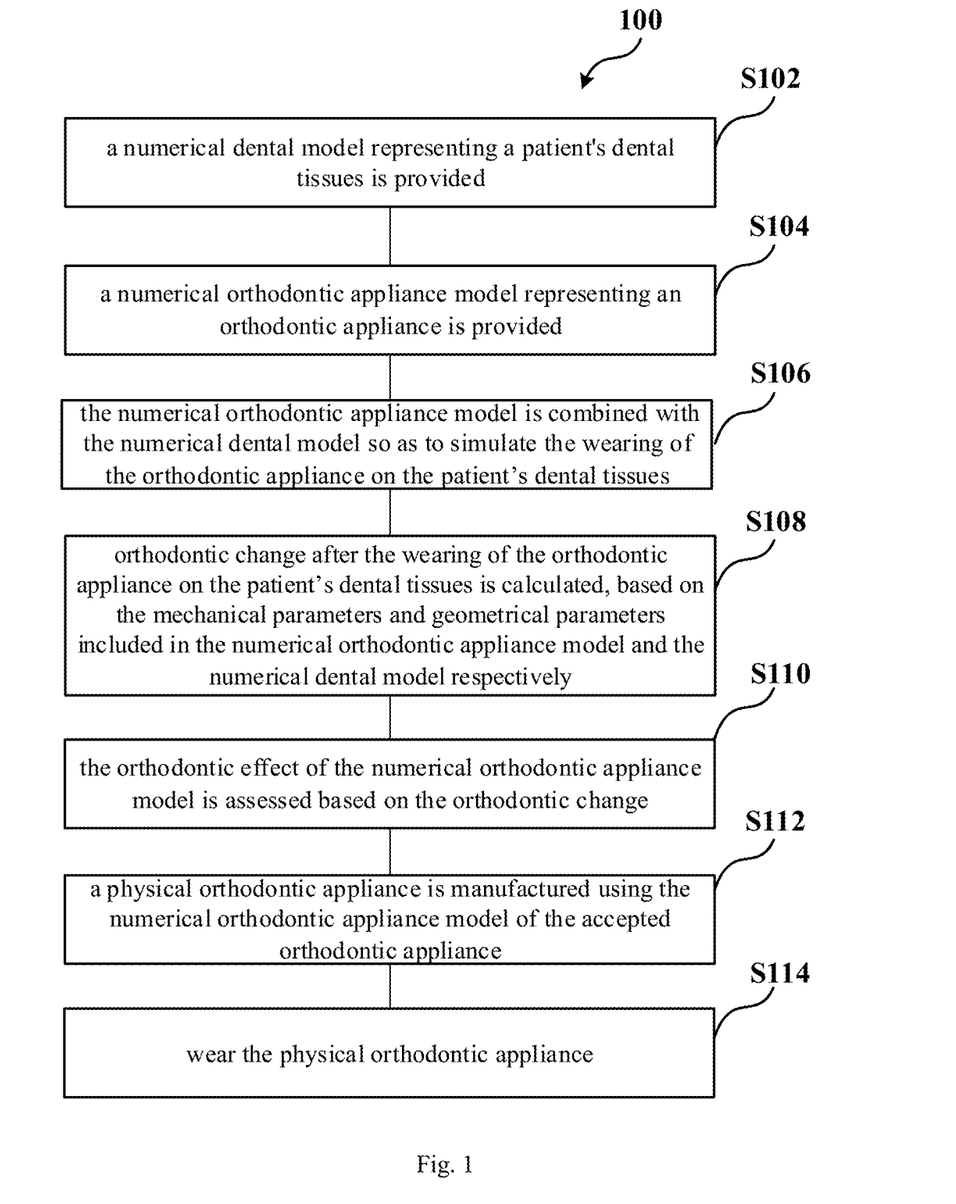
FIG. 1 illustrates an example of designing an orthodontic stage of an orthodontic appliance according to an embodiment of the present application.

FIG. 1 illustrates an example of an orthodontic stage 100 of orthodontic appliance design according to an embodiment of the present application, wherein a method of simulating orthodontic effect of an orthodontic appliance according to the present application is used.

In practical applications, the orthodontic appliance design may include an orthodontic treatment solution for correcting a patient's initial teeth state (i.e., uncorrected teeth state) to an expected target teeth state. An orthodontic treatment solution usually includes several successive orthodontic stages, each corresponding to an invisible orthodontic appliance. The patient may wear an invisible orthodontic appliance for a period of time (e.g., one or two weeks to one month) and then replace it with a different orthodontic appliance, so that the teeth are gradually aligned until the target teeth state is achieved.

As shown in FIG. 1, in step S102, a numerical dental model representing a patient's dental tissues is provided. The numerical dental model includes parameters regarding shape, position or arrangement (teeth shape, teeth arrangement, etc.) of the patient's dental tissues. In some examples, the numerical dental model may be the teeth arrangement of the patient before orthodontic treatment, i.e., at an initial teeth state. In other examples, the numerical dental model may be the intermediate teeth arrangement of the patient during the orthodontic treatment, i.e., at an intermediate teeth state.

A numerical dental model generally refers to a computerized data model used for guiding the manufacture of a physical dental model (i.e., a male mold), and is typically a virtual three-dimensional (3D) model for teeth geometry (also referred to as teeth arrangement). The virtual 3D model can be viewed, modified, or processed using a computer, workstation, or other data processing device with a graphical interface. The orthodontic state includes a series of modified teeth states, and each teeth state includes geometrical shapes of the teeth and positional relationships between the teeth during an orthodontic stage. Thus, each numerical dental model includes a data set representing the geometric shapes of the teeth and positional arrangements of the teeth, which may be referred to as geometrical parameters. Typically, the data model of teeth may include a model of the teeth and its surrounding tissue. For example, a tooth may include a crown portion, a neck portion, and a root portion; and the surrounding tissue may include gingiva, alveolar bone, etc. In some embodiments, a tooth may include a crown portion, and the surrounding tissue may include gingiva. In other embodiments, a tooth may include a crown portion, a neck portion, and a root portion, and the surrounding tissue may include gingiva and alveolar bone.

In one exemplary embodiment, a physical dental model (e.g., a gypsum dental model is produced by taking an impression) is first made based on a patient's current teeth state, or the state of the teeth and its surrounding tissue (e.g., gingiva, facial soft tissue). Then the physical dental model is scanned to generate a virtual teeth data model that represents the patient's basic teeth state. Of course, images of teeth or images of teeth and its surrounding tissue can be obtained directly by optical scanning, three-dimensional photographing, three-dimensional camera shooting, or medical CT scanning, and then the images can be processed by a computer to generate a virtual teeth data model of the basic teeth state. For example, a patient's teeth may be scanned by cone beam CT to obtain a teeth data model that includes crown, neck, root regions, etc. of teeth. This virtual teeth data model can be digitally processed and displayed, e.g., in a computer graphical interface.

Figure 2:
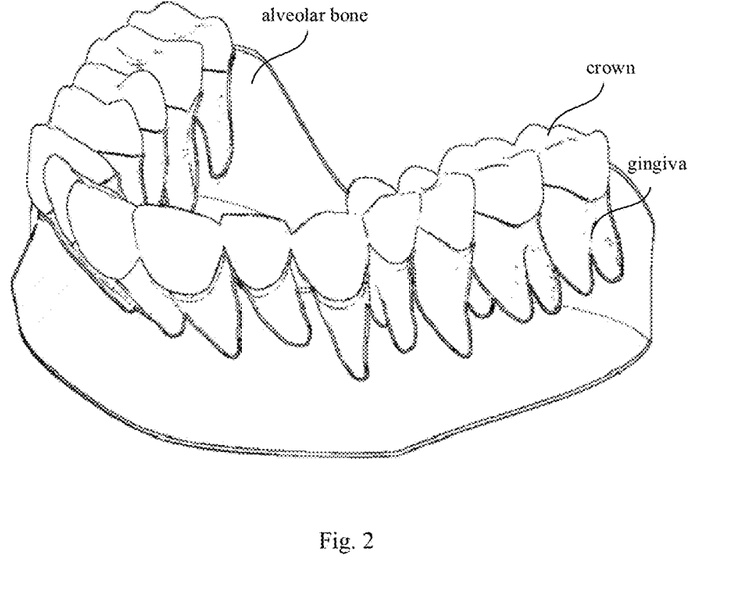
FIG. 2 illustrates an example of a numerical dental model according to an embodiment of the present application.

FIG. 2 illustrates an example of a numerical dental model according to an embodiment of the present application. As shown in FIG. 2, crowns, roots, periodontal ligaments, alveolar bones, etc. are all included in the numerical dental model.

In addition to the data representing the geometric shapes and positional arrangements of the teeth, the numerical dental model also includes mechanical parameters of a patient's dental tissues, such as elastic modulus, strain, etc. By adding mechanical parameters to the numerical dental model, the mechanical relationship between an orthodontic appliance and the numerical dental model can be expressed so that the effect of the orthodontic appliance on the teeth position of the numerical dental model can be further determined based on the mechanical relationship.

Figure 3:
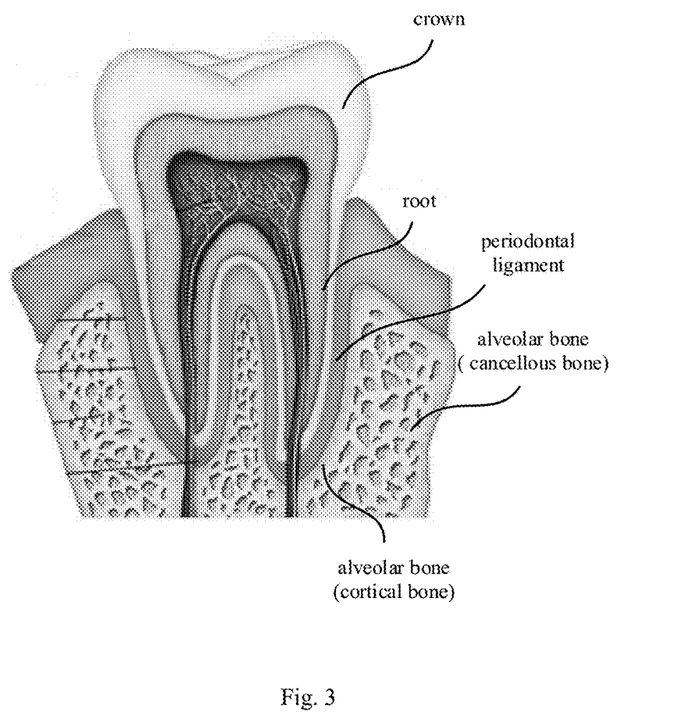
FIG. 3 illustrates a schematic diagram of a dental biological tissue structure.

FIG. 3 illustrates a schematic diagram of a dental biological tissue structure. As shown in FIG. 3, the crown, root, periodontal ligament, and alveolar bone (including cancellous bone and cortical bone) may have different biological tissue structures, and thus their biomechanical parameters (such as elastic modulus, Poisson's ratio, etc.) are different. In practical applications, the different biological tissue structures in the numerical dental model will be defined with different material properties, so that the numerical dental model has appropriate mechanical parameters for subsequent simulation calculations.

It will be understood that in many cases, the material properties of the dental biological tissue may vary with time and strain, which may affect the mechanical parameters in the numerical dental model. In some embodiments, the material properties and mechanical parameters of the dental biological tissue may be set as constants, i.e., regardless of the effect of time, strain, or other similar parameters on the material properties. This kind of processing can reduce the difficulty of simulation calculation. In other embodiments, the material properties and mechanical properties of the dental biological tissue may be set to vary with time and/or strain. Such processing may improve the accuracy of simulation. Regarding the material properties of the dental biological tissue, especially the influence of teeth movement on the material properties and mechanical parameters, references can be made to *Evaluation of long-term orthodontic tooth movement considering bone remodeling process and in the presence of alveolar bone loss using finite element method*, A. Zargham, et al., *Orthod Waves* (2016) and *Preliminary Study and Application of Bone Reconstruction Equations in Orthodontic Domains, Song Bangyong, Master's Thesis of Sichuan University*, May 10, 2005.

Still referring to FIG. 1, in step S104, a numerical orthodontic appliance model representing an orthodontic appliance is provided, the numerical orthodontic appliance model corresponding to an expected orthodontic state of the teeth and including mechanical parameters of the orthodontic appliance.

In some embodiments, the numerical orthodontic appliance model is obtained by the design of teeth arrangement according to clinical medical experience, and the model may correspond, for example, to an orthodontic stage of the orthodontic treatment solution. Similar to the numerical dental model, the numerical orthodontic appliance model reflects teeth arrangement at the expected orthodontic state. On the other hand, the mechanical parameters of the orthodontic appliance are usually dependent on the material used to make the appliance (i.e., the film material), which may be incorporated as a parameter during the model design. For example, different membrane materials may have different mechanical parameters (e.g., elastic modulus, Poisson's ratio, density, etc.). In some embodiments, the membrane material of the orthodontic appliance may be set as a constant. However, in other embodiments, the membrane material of the orthodontic appliance may also be configured to have varying mechanical parameters, such as a varying elasticity modulus, which is usually caused by stress relaxation. Accordingly, it is possible to determine how the mechanical parameters of the membrane material will vary by testing stress relaxation of the membrane material. This processing can improve the accuracy of simulation.

In some embodiments, the numerical orthodontic appliance model may be obtained by scanning a physical model of the corresponding orthodontic appliance. For example, in an orthodontic stage of the orthodontic treatment plan, a numerical dental model after changes of the teeth arrangement can be determined. Then, a male mold for the teeth can be made using the numerical dental model, and a physical model of the corresponding orthodontic appliance is made based on the male mold for teeth. Finally, the physical model can be scanned to obtain a numerical orthodontic appliance model. This processing takes the manufacturing errors occurred during the manufacture of the orthodontic appliance into account, thereby reducing the error in the subsequent simulation processing.

In other embodiments, the orthodontic appliance manufacturing process may also be simulated. For example, by simulating the membrane heating process, the thermoforming process for an orthodontic appliance, the cooling rebound process for an orthodontic appliance, and the cutting process for an orthodontic appliance, a numerical orthodontic appliance model for verifying the orthodontic effect can be generated based on the simulating results of the processes. This treatment can avoid the complex processing, such as manufacturing and scanning the physical model of the orthodontic appliance, and thereby saving the verification cost.

It should be noted that, an orthodontic appliance usually includes a part being put on the maxillary dentition and a part being put on the mandibular dentition, and the simulation and evaluation of the orthodontic effect by the two parts on maxillary and mandibular dentitions are usually carried out separately. Thus, the numerical dental model provided in step S102 may only include the maxillary dentition, and the numerical orthodontic appliance model provided in step S104 may only include an invisible appliance for the maxillary dentition. Alternatively, the numerical dental model provided in step S102 may only include the mandibular dentition, and the numerical orthodontic appliance model provided in step S104 may only include an invisible appliance for the mandibular dentition. Of course, it is also possible to provide both maxillary and mandibular dentitions and corresponding numerical orthodontic appliance models, and then perform subsequent simulations respectively. It is understood that, in some examples, it may also be possible to simulate and verify the orthodontic effect of only one tooth or several teeth, and the surrounding tissue in the maxillary dentition or mandibular dentition. Correspondingly, a partial model can be extracted from a portion of the numerical dental model for simulation.

Figure 4A:
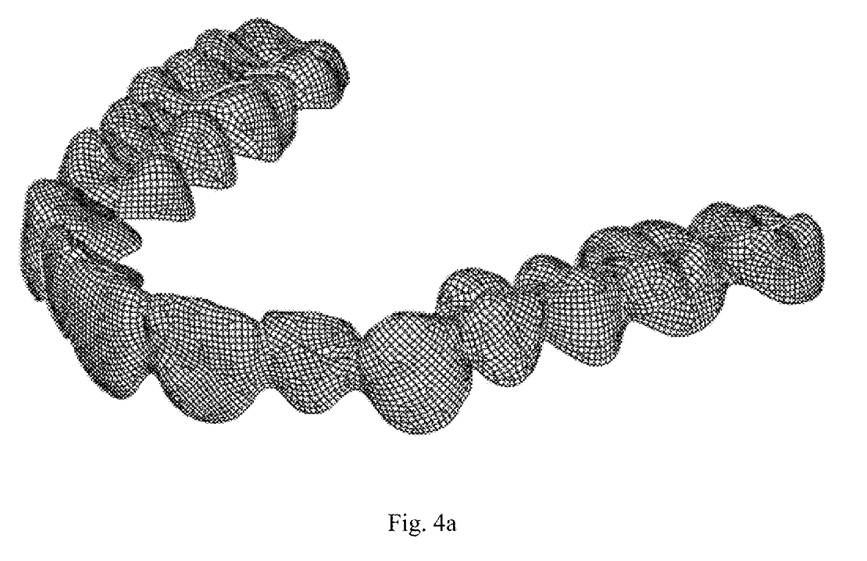
FIGS. 4a and 4b illustrate two examples of a numerical orthodontic appliance model.
Figure 4B:
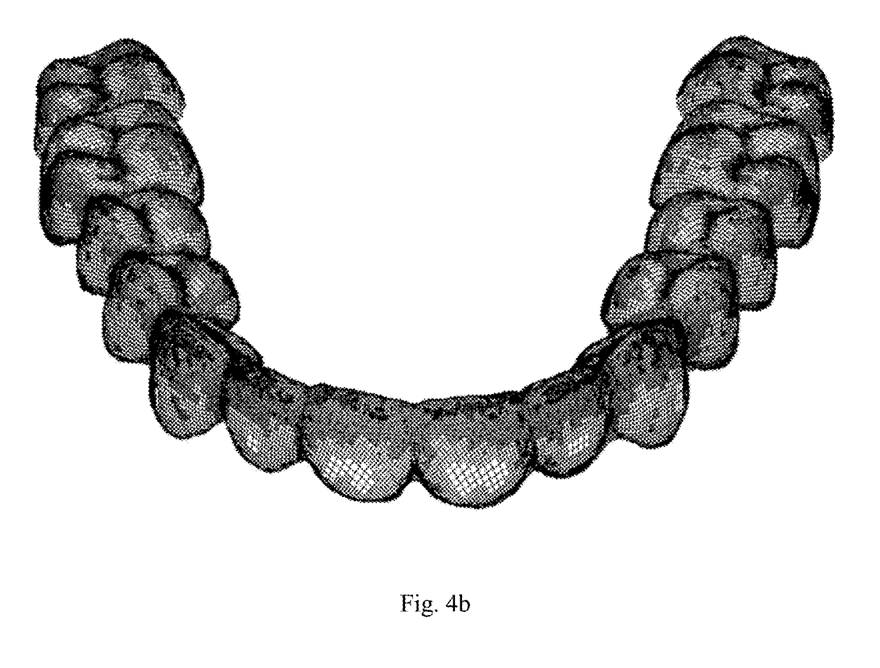

FIGS. 4a and 4b illustrate two examples of a numerical orthodontic appliance model. The example shown in FIG. 4a is an orthodontic appliance model divided into solid elements, and the example shown in FIG. 4b is an orthodontic appliance model divided into shell elements. It can be seen that the numerical orthodontic appliance model has been meshed into a finite element model, such that finite element calculations can be performed in the simulation processing.

Still referring to FIG. 1, in step S106, the numerical orthodontic appliance model is combined with the numerical dental model so as to simulate the wearing of the orthodontic appliance on the patient's dental tissues.

The numerical orthodontic appliance model represents the expected orthodontic state of teeth, and thus it does not exactly match the shape and arrangement of a patient's dental tissues before orthodontic treatment. Therefore, different methods can be used to combine the numerical orthodontic appliance model with the numerical dental model. In some embodiments, the process of wearing the appliance may be simulated first, and the contact of the numerical orthodontic appliance model with the numerical dental model may be determined based on the simulation result of wearing. In other embodiments, it is also possible to determine the contact condition of the orthodontic appliance with the dental tissues through an algorithm defined by the finite element contact, other than simulating the wearing process.

Figure 5A:
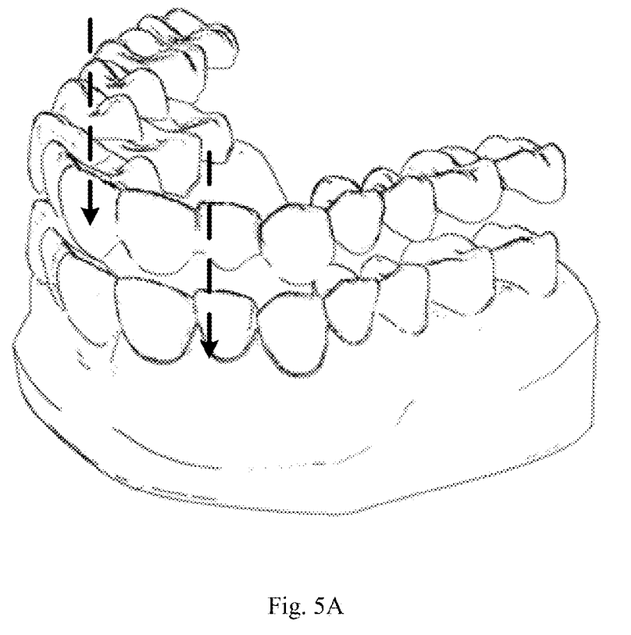
FIGS. 5a to 5c illustrate an example process of wearing a numerical orthodontic appliance model on a numerical dental model.
Figure 5B:
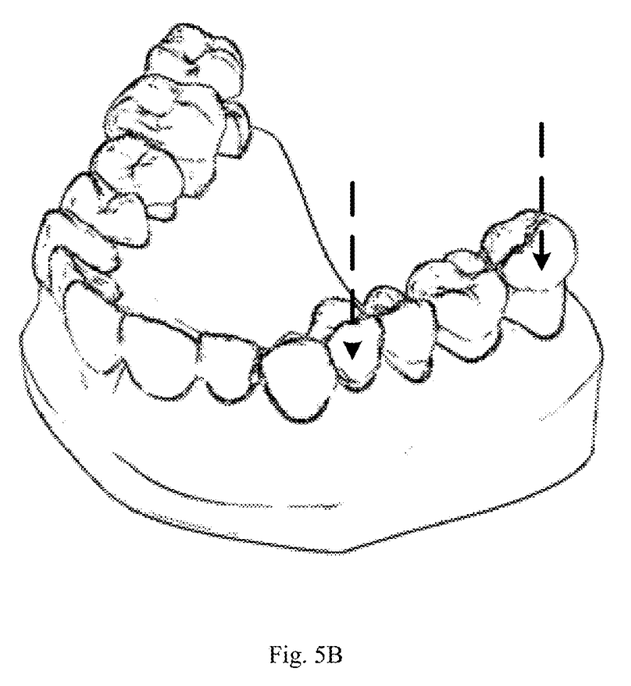
Figure 5C:
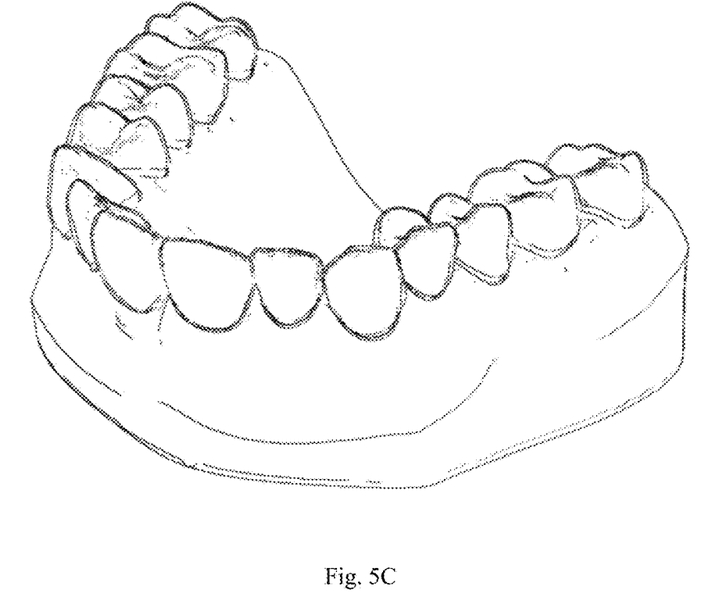

FIGS. 5a to 5c illustrate an example process of wearing a numerical orthodontic appliance model on a numerical dental model.

As shown in FIG. 5a, a force is exerted on a region of the anterior teeth so that the orthodontic appliance model and the dental model are combined with each other at the region. Then, as shown in FIG. 5b, a force is gradually exerted on a region of the posterior teeth so that the orthodontic appliance model and the dental model are combined with each other at the region. During this period, the force exerted on the region of the anterior teeth may remain or be withdrawn. Finally, as shown in FIG. 5c, after the wearing operation is completed, the previously exerted pressure can be withdrawn, and the orthodontic appliance model produces orthodontic force on the dental model, which causes deformation of the periodontal tissue. A resisting force caused by the periodontal tissue deformation mechanically balances the orthodontic force, thereby determining change of the teeth arrangement in the dental model.

The analysis about the contact of the dental model with the orthodontic appliance model may include the following steps.

1) Creating a Model and Meshing

Normally, the creation of model includes setting ID, type, material property, etc. of an element. Two contacting objects can be divided into meshes with an appropriate element type. For a dental model, if there are small pores, it is preferable to carry out the processing of filling; if there are sharp angles, it is preferable to carry out the processing of smoothing optimization.

2) Identifying Contact or Contact Pairs

A contact or contact pair is created by defining a target element and a contact element, and the target element and the contact element are associated with each other with the definition of the contact ID. Due to the diversity of geometric models and potential deformations, the same area of a contact surface may sometimes contact with multiple target surfaces, and multiple contact should be defined accordingly.

3) Defining a Rigid Target Surface

The crown surface of each tooth in the dental model is defined as a rigid target surface. For example, if there are 14 teeth, set 14 independent rigid target surfaces.

4) Defining the Contact Surface of a Non-Rigid Object

The inner surface of the orthodontic appliance model is integrally defined as a contact surface.

5) Setting Contact or Contact Pairs, and Controlling the Contact Elements.

First, select a contact algorithm. In the present application, a preferred algorithm may be an extended Lagrange Multiplier Method or a Penalty method. The former is obtained through correcting parameters applying an iterative method to the latter, and thus the former is more powerful but easier to render the deformation of the meshes distorted excessively. The actual application is decided according to actual situation. The Penalty Method is a default method, and its principle is to preform penetration compensation, wherein the compensated restoring force is in proportion to the penetration distance, and the solution of non-linear programming problems is transformed into solution of a series of unconstrained extreme problems.

And then determine contact stiffness, and adjust penetration tolerance, penetration compensation, and other initial contact parameters. In general, a sufficiently large contact stiffness should be selected to ensure that the contact penetration is small enough to be acceptable, while the contact stiffness should be made small enough to avoid causing ill-posed problems of the stiffness matrix, thereby ensuring convergence.

Some other settings are determined thereafter, including selecting friction types and friction coefficients (including dynamic and static friction coefficients), selecting surface action modes, selecting action modes influenced by thickness, calculating step control, and options of active/inactive elements.

In the process of simulating the combination of numerical orthodontic appliance model and the numerical dental model, the following technical points shall be considered.

1) Regarding the Mechanical Model

Solid elements and shell elements are used to divide the orthodontic appliance into meshes. In order to ensure the accuracy of calculation, mesh refinement is performed on the area having a larger curvature when the orthodontic appliance is divided into meshes. Mesh refinement usually can be performed automatically by a simulation software, or can be manually selected or set by a designer. At the same time, in order to reduce the simulating time, the numerical dental model can be set as a rigid object in the simulation process, regardless of the biomechanical reaction generated by gingival tissue. Since the wearing process of an orthodontic appliance is very short and is carried out at room temperature, the material properties of the numerical orthodontic appliance model are primarily focused on elasticity, and the viscous property may be ignored. Therefore, during the simulation analysis, the material model of the numerical orthodontic appliance model can be set as elastic-plastic. In practical applications, LS-DYNA general software can be used for simulation analysis. LS-DYNA is an explicit finite element solution tool with plentiful contact elements. For contact problems for models with complex shapes, LS-DYNA can solve the problems rapidly with high precision.

The constraints of a dental model can be defined in various ways. In an example, each tooth (including its crown and root) in the dental model can be set as a rigid object and contact between adjacent teeth can be defined as rigid contact, so as to ensure that there is no interference between adjacent teeth; a full constraint for six degrees of freedom (DOFs) can be applied for a portion or entire of the alveolar bone in the model; finite element nodes are shared between the root and the periodontal ligament, and the tied contact is replaced by way of sharing nodes; and finite element nodes are shared between the periodontal ligament and the alveolar bone, and the tied contact is replaced by way of sharing nodes. In another example, the finite element nodes are not shared between the root and the periodontal ligament, and the nodes are not shared between the periodontal ligament and the alveolar bone either; and the tied contact is defined between different regions to tie the contact surface completely.

The parameters required in the mechanical model may include: friction coefficient between the orthodontic appliance and the dental tissues; and the density, elastic modulus, Poisson's ratio, yield strength (considered in an elastic-plastic model), etc. of the orthodontic appliance at room temperature; and the density, elastic modulus, Poisson's ratio, etc. of the dental tissues at room temperature.

2) Regarding the Wearing Process

In the process of wearing, it is difficult to calculate the contact behavior between the orthodontic appliance model and the dental model for it involves a rigid to non-rigid coupling dynamic contact problem of a nonlinear structure. The convergence of the calculation is poor, and it is easy to occur contact penetration. In general, the contact condition can be improved by adjusting the contact stiffness, penetration tolerance and other parameters. In addition, it is necessary to properly set the wearing path of the orthodontic appliance model to ensure that the orthodontic appliance model can be successfully worn onto the dental model. According to the principle of relative movement, during the wearing of the orthodontic appliance model, the orthodontic appliance model can be set to remain stationary while moving conditions can be applied to the dental model. For example, the orthodontic appliance model may be moved in the direction shown in FIGS. 5a and 5b. In this method, the boundary constraint conditions are: limiting the DOFs of the dental model in all directions except for the wearing direction; limiting all the DOFs of the orthodontic appliance model at the selected nodes; limiting the DOFs of the orthodontic appliance model at other selected nodes in all directions except for the wearing direction; and after the contact is initially established, releasing the limitation on all the nodes of the orthodontic appliance model to perform stress redistribution.

Alternatively, it is also possible to set the dental model to remain stationary and apply moving conditions to the orthodontic appliance model to achieve relative movement between the two models and thereby simulate the wearing process. Simulation of the whole wearing process can be achieved using a finite element simulation software. In this method, the boundary constraint conditions are: a number of nodes are randomly selected from each tooth geometry of the orthodontic appliance model and set to be rigidly connected together; constant loads in the wearing direction of the orthodontic appliance model; and after the contact is initially established, releasing the limitation on all the nodes of the orthodontic appliance model to perform stress redistribution.

In other embodiments, rather than performing simulation of the wearing process, it is also possible to determine the real contact condition between the deformed orthodontic appliance and the dental tissues with a calculation method defined by finite element contact, thereby simulating the wearing state of the orthodontic appliance model on the dental model.

An available calculation method defined by finite element contact is provided as follows. First, the inner surface of the orthodontic appliance model is preliminarily fitted in geometry with the outer surface of the dental model, for example, using a best fit alignment algorithm. Then, normal loads along the outer surface of the dental model are applied towards the inner surface of the orthodontic appliance model using an explicit algorithm, so that the inner surface of the orthodontic appliance is completely coincident with the outer surface of the dental model, or is positioned in a normal direction along the outer surface of the dental model. After that, the previously applied load is slowly removed by using an explicit algorithm, and an initial contact between the inner surface of the orthodontic appliance model and the outer surface of the dental model is established. Finally, the stress redistribution of the orthodontic appliance model is calculated using an implicit algorithm, so that the contact force between the orthodontic appliance model and the dental model is thus completed. In this method, the boundary constraint conditions are: a number of nodes are randomly selected from each tooth geometry of the orthodontic appliance model and set to be rigidly connected together; at the same time, several other nodes not having initial penetration with the teeth are selected from the location of each tooth geometry of the orthodontic appliance model, and are applied with a full constraint of six DOFs; and after the contact is initially established, releasing the limitation on all the nodes of the orthodontic appliance model to perform stress redistribution.

Another available calculating method defined by the finite element contact is provided as follows. First, a virtual material model is temporarily provided for the orthodontic appliance model. For example, the orthodontic appliance model is set to be an ideal temperature memory object, and its material property is set to be softened with increasing temperature. Then, the inner surface of the orthodontic appliance model is preliminarily fitted in geometry with the outer surface of the dental model. Next, the temperature of the orthodontic appliance model is raised to soften it and render it ideally attached to the teeth surface of the dental model, and then the temperature is lowered to the initial temperature. According to the predefined virtual material property of the orthodontic appliance model, i.e., the orthodontic appliance model is an ideal temperature memory object, the orthodontic appliance model becomes hard and attempts to return to the original geometrical position. In this process, the contact force against the dental model occurs, and thus the contact definition is completed. In this method, the boundary constraint conditions can be obtained according to the same boundary constraint conditions mentioned in the previous paragraph.

In practice, other methods can also be used to simulate the wearing process. For example, the inner surface of the numerical orthodontic model may be preliminarily fitted in geometry with the outer surface of the numerical dental model, and then the inner surface of the numerical orthodontic appliance model and the outer surface of the numerical dental model may be cut, and corresponding contact pairs may be set. Afterwards, by a contact manner of interference fit and through parameter settings such as penetration restoring, penetration compensating, etc., the inner surface of the numerical orthodontic appliance model is displaced and thus completely coincided with the outer surface of the numerical dental model, whereas the contact definition is completed. The boundary constraint conditions in the method are: several nodes not having initial penetration with the teeth are selected from the location of each tooth geometry of the orthodontic appliance model, and are applied with a full constraint of six DOFs; and after the contact is initially established, releasing the limitation on all the nodes of the orthodontic appliance model to perform stress redistribution.

It can be seen that, after combination of the numerical orthodontic appliance model and the numerical dental model, the boundary constraint conditions of the two models can then be determined.

Still referring to FIG. 1, then in step S108, orthodontic change after the wearing of the orthodontic appliance on the patient's dental tissues is calculated, based on the mechanical parameters and geometrical parameters included in the numerical orthodontic appliance model and the numerical dental model respectively.

In particular, after combining the numerical orthodontic appliance model with the numerical dental model, the morphologies of both the two models have changed so that forces are generated between them. That is, an orthodontic force applied by the numerical orthodontic appliance model to the numerical dental model, and a resisting force applied by the numerical dental model to the numerical orthodontic appliance model in an opposite direction. These two forces make the shapes and/or positions of different regions of the two models change, so that mechanical equilibrium can be achieved in different regions. For example, the orthodontic force applied by the orthodontic appliance may cause a region of the numerical dental model to move in an opposite direction or to depress in an opposite direction, causing deformation of a corresponding position of the periodontal tissue. The deformation on the numerical dental model generates stress, which is used as the resisting force to balance the orthodontic force. In general, teeth have high hardness, and may be considered to be substantially unchanged in the course of orthodontic treatment. Conversely, periodontal tissues (such as periodontal ligament and alveolar bone) have lower hardness, and can be easily deformed in orthodontic treatment. Additionally, the deformation of the periodontal tissues during orthodontic treatment is the main cause of teeth movement in the treatment. Therefore, in practical applications, the deformation of periodontal tissues is the main basis for the evaluation of orthodontic effect.

In practical applications, a finite element calculation and simulation software can be used to calculate the mechanical equilibrium between the two models. For example, according to the mechanical parameters and geometrical parameters included in the numerical orthodontic appliance model and the numerical dental model respectively, as well as the boundary constraints obtained after the wearing simulation, combined with the difference between the initial state (shape and teeth arrangement) of the two models, the finite element calculation software can iteratively calculate the deformation on the two models until the orthodontic force provided by the numerical orthodontic appliance model and the resisting force caused by the deformation of the periodontal tissues as represented by the numerical dental model reach a mechanical equilibrium state. When a mechanical equilibrium state is reached, the movement of the patient's dental tissues as represented by the numerical dental model can be regarded as the orthodontic change.

As mentioned above, in some embodiments, the mechanical parameters included in the two models may vary with time and/or strain, or with the change of other parameters. In this case, the mechanical parameters can be expressed as a function of these variables. For example, the elastic modulus of membrane material of the orthodontic appliance can be expressed as $E(t)=g(t)*E_0$, wherein $E_0$ represents an initial value of the elastic modulus, and $g(t)$ represents a coefficient of the elastic modulus of the membrane material varying with time, which can be determined by a stress relaxation test on the membrane material. For another example, the elastic modulus of the periodontal tissue material can be expressed as $E(t)=f(s, t)*E_0$, wherein $E_0$ represents an initial value of the elastic modulus, and $f(s, t)$ represents a coefficient of the elasticity modulus of the periodontal tissue material varying with time and strain. It will be understood that the elastic modulus of different regions in the numerical dental model may be different, because the elastic modulus of the periodontal tissue material may vary with strain. Similarly, other mechanical parameters, such as Poisson's ratio, can also vary with time, which will not be repeated herein.

Considering the change of mechanical parameters with time, a certain time interval (for example, every other day) can be set to determine updated mechanical parameters. In this way, the updated mechanical parameters can be used to recalculate the deformation of the periodontal tissue in the patient's mandible and maxilla until the orthodontic force provided by the numerical orthodontic appliance model and the resisting force caused by the deformation of the periodontal tissues as represented by the numerical dental model achieve a new mechanical equilibrium state. This dynamic equilibrium calculation can reflect the actual orthodontic effect of the orthodontic appliance more accurately.

It is to be understood that, if the two models in the mechanical equilibrium state during a certain period of time are coincide with the expected orthodontic state, the numerical orthodontic appliance model can be used to make a physical model of an orthodontic appliance. However, if the two models fail to achieve any mechanical equilibrium states that are coincide with the expected orthodontic state after a predetermined period of time, such as one to two weeks or one month, the numerical orthodontic appliance model fails to meet the orthodontic requirements and needs to be modified.

Figure 6:
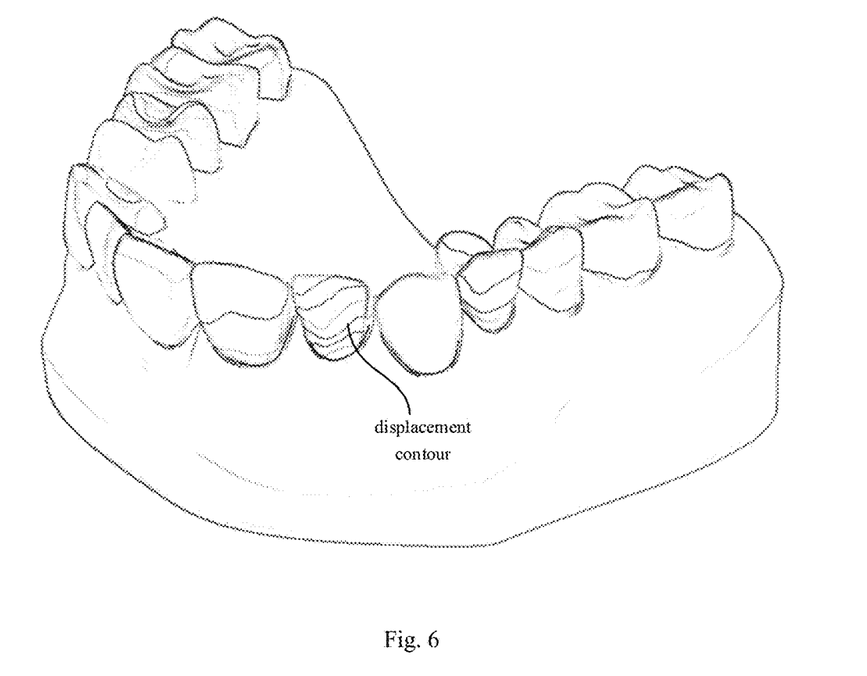
FIG. 6 illustrates a numerical dental model that includes orthodontic change.

In some embodiments, the orthodontic change calculated in step S108 may be output and displayed, for example, by a computer graphical interface showing a numerical dental model that includes orthodontic change. FIG. 6 illustrates a numerical dental model that includes orthodontic change. As shown in FIG. 6, the orthodontic changes are mainly the displacement of different teeth and different portions of a tooth, which are displayed on the numerical dental model in form of displacement contours. Since there are many ways to move a tooth, which may either translate in a certain direction, or rotate around a rotation axis or axes, the displacement of different teeth or different portions of the same tooth can be identical or different.

In some embodiments, the orthodontic change also includes disappearance or generation of a portion of the periodontal tissue. For example, a portion of the periodontal tissue (e.g., alveolar bone) may disappear or be generated due to an orthodontic force, which makes the shape of the periodontal tissue change slightly. The change of shape can also be represented on the numerical dental model.

In step S110, the orthodontic effect of the numerical orthodontic appliance model is assessed based on the orthodontic change. In some embodiments, the orthodontic change is compared with the expected orthodontic state that corresponds to the orthodontic appliance. The orthodontic appliance will be rejected when the difference between the orthodontic change and the expected orthodontic state exceeds a predetermined tolerance, for example, the difference between the amount of teeth displacement and the expected displacement is greater than 30% (compared to the expected displacement). On the contrary, the orthodontic appliance will be accepted when the difference between the orthodontic change and the expected orthodontic state does not exceed the predetermined tolerance.

In some embodiments, in step S112, a physical orthodontic appliance can be manufactured using the numerical orthodontic appliance model of the accepted orthodontic appliance. Thereafter, in step S114, the patient can wear the physical orthodontic appliance for orthodontic treatment.

In other embodiments, for the rejected orthodontic appliance, the numerical orthodontic appliance model can be modified according to the orthodontic change calculated in step S108. For example, if the calculated value of the orthodontic change is less than a value of the expected orthodontic state, the difference in shape and arrangement between the numerical orthodontic appliance model and the numerical dental model in some regions may be increased, or a material with a larger elasticity modulus may be used, so as to increase the orthodontic force of orthodontic appliance, such that the orthodontic effect of the orthodontic appliance can meet the expected requirements. On the contrary, if the calculated value of the orthodontic change is greater than the value of the expected orthodontic state, the difference in shape and arrangement between the numerical orthodontic model and the numerical dental model in some regions may be reduced, or a material with a smaller elasticity modulus may be used, so as to reduce the orthodontic force of the orthodontic appliance. It will be understood that the modification of the above-mentioned orthodontic appliance may be repeated iteratively for several times, so that the orthodontic effect of the orthodontic appliance is gradually approaching the expected orthodontic state.

After that, a male mold of the orthodontic appliance can be made based on the numerical dental model that conforms to the expected orthodontic state. Preferably, the male mold of the orthodontic appliance may be fabricated through a process of rapid prototyping. Rapid prototyping technology may include the following several kinds of typical forming processes: Stereo Lithography Apparatus (SLA), Laminated Object Manufacturing (LOM), Selected Laser Sintering (SLS), Fused Deposition Modeling (FDM), Three Dimensional Printing (3DP) and so on. Regarding the modeling materials, organic polymer materials, such as light curing resin, nylon, wax, etc. are normally used. The Stereo Lithography Apparatus uses laser to radiate the light curing resin point by point, thereby inducing chemical reactions occurred in the material and thus curing the material for modeling. The Laminated Object Manufacturing uses laser to cut foil materials (paper, ceramic foil, metal foil, etc.), which are bound by a hot melt adhesive under pressure and heat transfer effect of a heat roller and modeled through lamination. The Selected Laser Sintering uses laser to radiate and melt powder materials point by point, or melt a solid adhesive coated outside of powder materials to couple the materials to an object. The Fused Deposition Modeling delivers thermoplastic molding materials continuously into a nozzle, inside which the materials are heated and then sprayed to gradually stack into an object. The Three Dimensional Printing uses a method similar to ink-jet printing that sprays molten material to stack into an object, or spray binder point by point to bind the powder materials to an object.

The orthodontic appliance may then be made based on the male mold of the orthodontic appliance. In a specific embodiment, the appliance membrane consisting of transparent polymeric material (non-rigid polymer, such as polycarbonate) is pressed and molded upon the physical dental model to form a shell by means of a positive pressure or negative pressure press-molding technique with a thermoforming unit, thereby manufacturing an orthodontic appliance. However, the method of manufacturing an orthodontic appliance based on the dental model of the present application is not limited to thermoforming process, and other suitable methods can also be applied to manufacture a physical orthodontic appliance.

In some embodiments, a data model of the orthodontic appliance may also be generated based on the numerical dental model that conforms to the expected orthodontic state. Thereafter, an orthodontic appliance is made based on the generated data model of the orthodontic appliance. For example, an orthodontic appliance may be manufactured based on a rapid prototyping process.

The embodiment shown in FIG. 1 involves a method of simulating orthodontic effect of an orthodontic appliance in one orthodontic stage of the orthodontic treatment solution according to the present invention. In practice, the orthodontic effect of the orthodontic appliance can be simulated and evaluated in other ways, or the simulation results can be further used to guide the design and manufacture of the orthodontic appliance.

Figure 7:
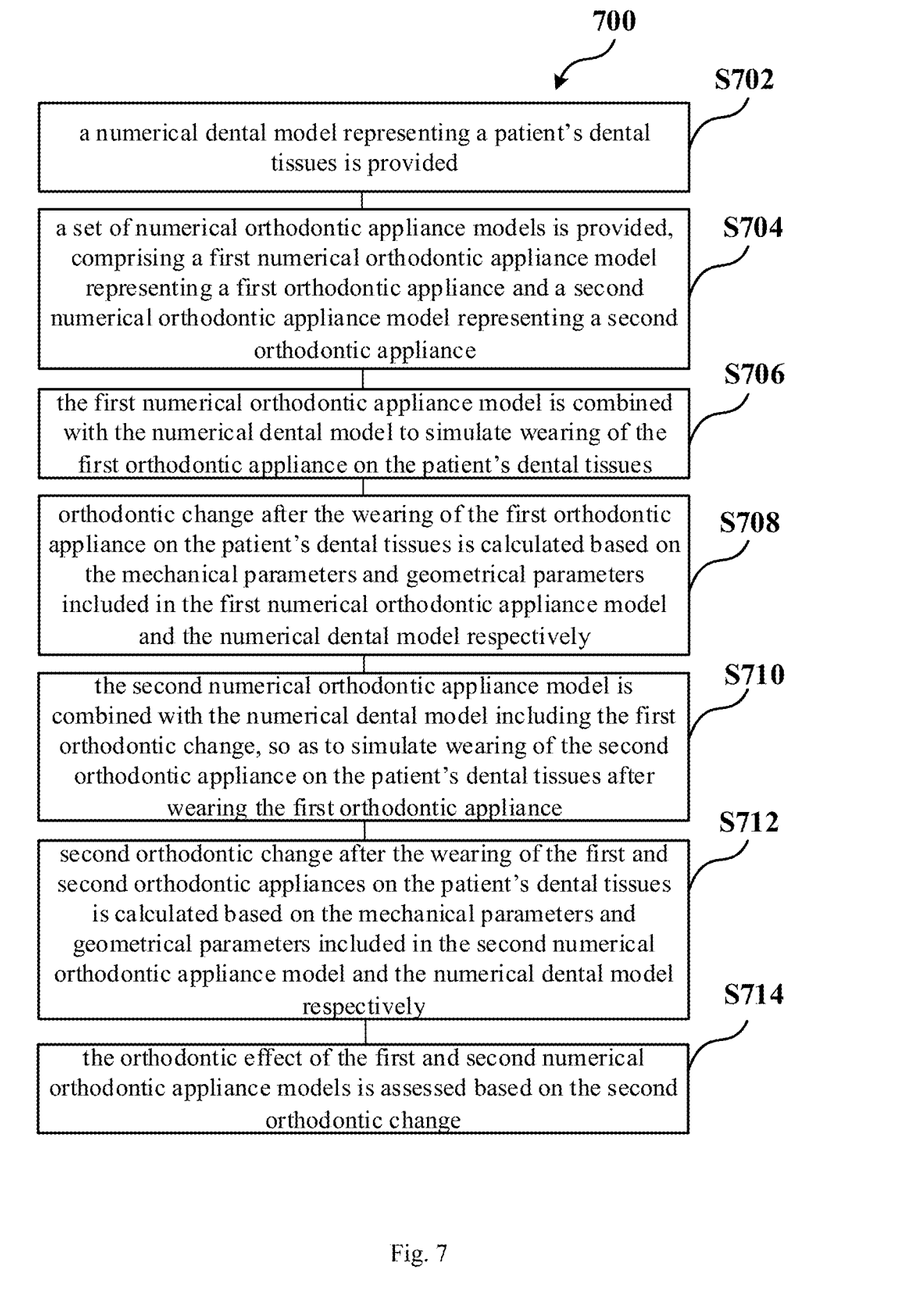
FIG. 7 illustrates a method of numerically simulating the orthodontic effect of an orthodontic appliance according to another embodiment of the present application.

FIG. 7 illustrates a method 700 for numerically simulating orthodontic effect of an orthodontic appliance according to another embodiment of the present application.

As shown in FIG. 7, in step S702, a numerical dental model representing a patient's dental tissues is provided, wherein the numerical dental model comprises mechanical parameters and geometrical parameters of the patient's dental tissues. In step S704, a set of numerical orthodontic appliance models is provided, wherein the set of numerical orthodontic appliance models comprises at least a first numerical orthodontic appliance model representing a first orthodontic appliance and a second numerical orthodontic appliance model representing a second orthodontic appliance; wherein the first orthodontic appliance corresponds to a first expected orthodontic state, the second orthodontic appliance corresponds to a second expected orthodontic state after the first expected orthodontic state, and the first numerical orthodontic appliance model includes mechanical parameters and geometrical parameters of the first orthodontic appliance, and the second numerical orthodontic appliance model includes mechanical parameters and geometrical parameters of the second orthodontic appliance. In step S706, the first numerical orthodontic appliance model is combined with the numerical dental model to simulate wearing of the first orthodontic appliance on the patient's dental tissues. In step S708, orthodontic change after the wearing of the first orthodontic appliance on the patient's dental tissues is calculated based on the mechanical parameters and geometrical parameters included in the first numerical orthodontic appliance model and the numerical dental model respectively. In step S710, the second numerical orthodontic appliance model is combined with the numerical dental model including the first orthodontic change, so as to simulate wearing of the second orthodontic appliance on the patient's dental tissues after wearing the first orthodontic appliance. In step S712, second orthodontic change after the wearing of the first orthodontic appliance and the second orthodontic appliance on the patient's dental tissues is calculated based on the mechanical parameters and geometrical parameters included in the second numerical orthodontic appliance model and the numerical dental model respectively. In step S714, the orthodontic effect of the first and second numerical orthodontic appliance models is assessed based on the second orthodontic change.

It can be seen that, in the above method, the state (e.g., arrangement) of the numerical dental model after orthodontic treatment of one orthodontic stage can be used as an initial state of the next orthodontic stage, so as to evaluate the orthodontic effect of the next numerical orthodontic appliance model for the numerical dental model. In this way, the digital orthodontic appliance models of all orthodontic stages in the orthodontic treatment can be sequentially applied to the digital dental models, thereby assessing the orthodontic effect of the entire treatment.

Figure 8:
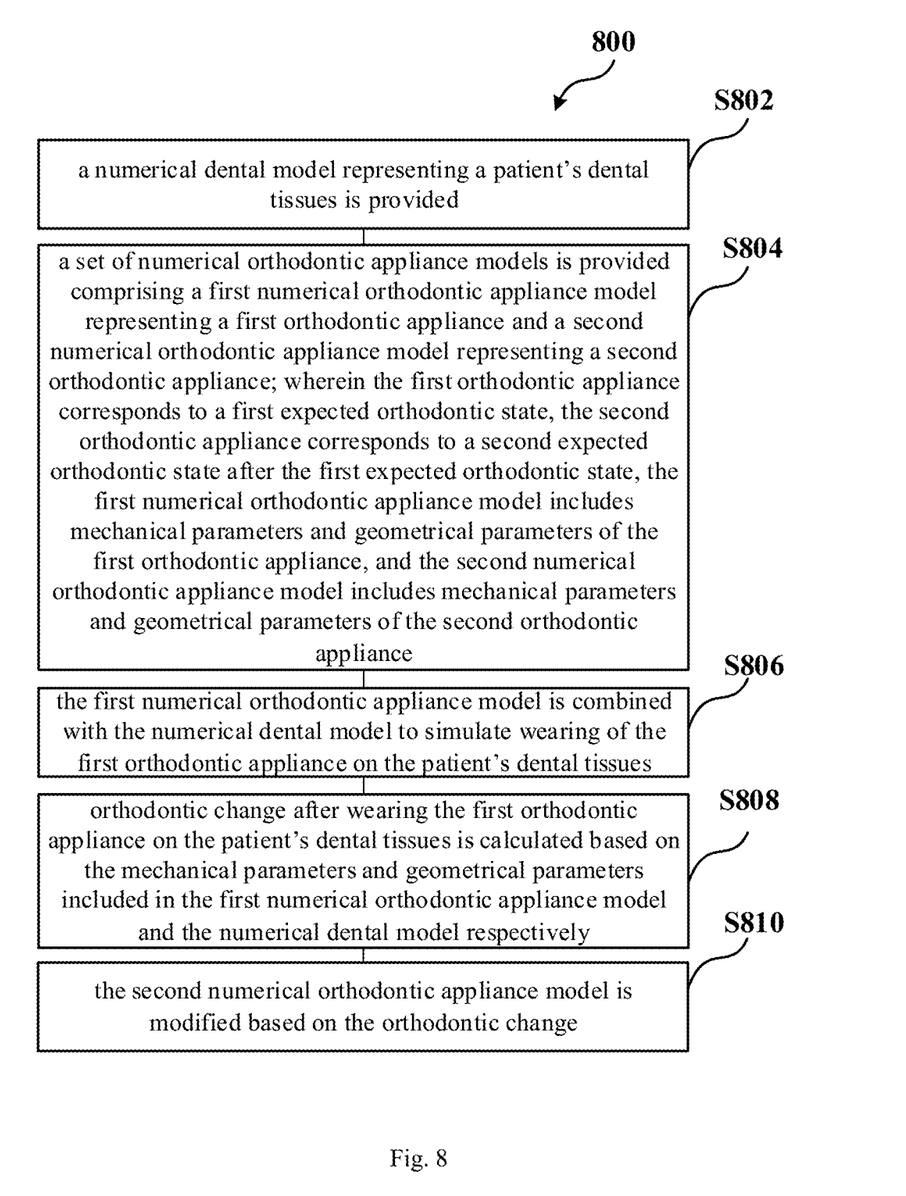
FIG. 8 illustrates a method of numerically simulating the orthodontic effect of an orthodontic appliance according to yet another embodiment of the present application.

FIG. 8 illustrates a method 800 for numerically simulating orthodontic effect of an orthodontic appliance according to yet another embodiment of the present application.

As shown in FIG. 8, in step S802, a numerical dental model representing a patient's dental tissues is provided, wherein the numerical dental model comprises mechanical parameters and geometrical parameters of the patient's dental tissues. In step S804, a set of numerical orthodontic appliance models is provided, wherein the set of numerical orthodontic appliance models comprises at least a first numerical orthodontic appliance model representing a first orthodontic appliance and a second numerical orthodontic appliance model representing a second orthodontic appliance; wherein the first orthodontic appliance corresponds to a first expected orthodontic state, the second orthodontic appliance corresponds to a second expected orthodontic state after the first expected orthodontic state, the first numerical orthodontic appliance model includes mechanical parameters and geometrical parameters of the first orthodontic appliance, and the second numerical orthodontic appliance model includes mechanical parameters and geometrical parameters of the second orthodontic appliance. In step S806, the first numerical orthodontic appliance model is combined with the numerical dental model to simulate wearing of the first orthodontic appliance on the patient's dental tissues. In step S808, orthodontic change after wearing the first orthodontic appliance on the patient's dental tissues is calculated based on the mechanical parameters and geometrical parameters included in the first numerical orthodontic appliance model and the numerical dental model respectively. In step S810, the second numerical orthodontic appliance model is modified based on the orthodontic change.

In some embodiments, assessing the orthodontic effect of the first and second numerical orthodontic appliance models based on the second orthodontic change comprises: comparing the second orthodontic change with a second expected orthodontic state corresponding to the second orthodontic appliance; and rejecting the first and/or second orthodontic appliances when difference between the second orthodontic change and the second expected orthodontic state exceeds a predetermined tolerance; and accepting the first and/or second orthodontic appliances when the difference between the second orthodontic change and the second expected orthodontic state does not exceed the predetermined tolerance.

It can be seen that the numerical orthodontic appliance models at the different orthodontic stages of orthodontic treatment can be generated step by step. That is, for example, a first numerical orthodontic appliance model of a first orthodontic stage is initially generated, and then its influence on the numerical dental model is simulated, and a numerical dental model is obtained after the treatment of the first orthodontic stage. Thereafter, a numerical orthodontic appliance model of a second orthodontic stage can be generated based on the numerical dental model after the first orthodontic stage. The above steps can be repeated until the final orthodontic state of the numerical dental model satisfies the expected orthodontic effect. It can be seen that, such a design and simulation method takes into account the actual orthodontic effect of the numerical orthodontic appliance model, and can dynamically modify the orthodontic treatment solution according to the orthodontic effect, thereby significantly improving the orthodontic results.

A variety of alternative components, modified components or equivalent components may be used in place of the above-mentioned components. In addition, the technique described herein may be implemented in hardware or software, or in combination thereof. The technique may also be implemented by a computer program executable on a programmable computer, which includes a processor, a processor-readable storage medium (including volatile and non-volatile memory and/or storage elements) as well as matched input and output devices. The program code is applied to the data input through the input means to execute its function and generate output information. The output information can be applied to one or more output devices. Each program can be written in advanced processes or object-oriented programming languages in order to cooperate with the computer system. However, these programs can also be achieved through assembly or machine language if necessary. In any case, the language may be a compiled or interpreted language. Each of these computer programs may be stored in a storage medium or device (e.g., a CD-ROM, a hard disk, or an magnetic disk) that is readable by a general purpose or a dedicated programmable computer and, when being read by a computer to execute the process, it can be configured and thus operate the computer. The system can also be implemented as a computer readable storage medium in which a computer program is configured, and the storage medium as configured allows the computer to operate in a specific and predetermined manner.

While various aspects and embodiments of the present application are disclosed herein, other aspects and embodiments will be apparent to those skilled in the art. The various aspects and examples disclosed herein are for illustrative purposes only and are not intended to be limiting. This application is intended to cover any and all modifications and variations of the various embodiments of the present application. The scope and spirit of the present application are determined only by the appended claims.

Likewise, each of the graphs may show an exemplary architecture or other configuration of the disclosed methods and systems, and may facilitate understanding of the features and functions that included in the disclosed methods and systems. The claimed invention is not limited to the exemplary architecture or configuration shown, and the desired features may be implemented with various alternative architectures and configurations. In addition, for the flowcharts, functional descriptions, and method claims, the order of the blocks given herein should not be limited to the same order to perform the functions as implemented in the various embodiments, unless explicitly stated in the context.

Unless expressly stated, the terms and phrases used herein and variations thereof should be construed broadly, rather than restrictively. In some embodiments, the existing of the scalable terms and phrases such as "one or more," "at least", "but not limited to" or other similar wordings shall not be construed that it is intended or required to narrow the situations in the examples without the scalable terms.

What is claimed is:

1. A method for numerically simulating orthodontic effect of an orthodontic appliance, comprising the following steps:
   providing a numerical dental model representing a patient's dental tissues, wherein the numerical dental model comprises mechanical parameters and geometrical parameters of the patient's dental tissues;
   providing a numerical orthodontic appliance model representing the orthodontic appliance, and the numerical orthodontic appliance model comprising mechanical parameters and geometrical parameters of the orthodontic appliance;
   combining the numerical orthodontic appliance model with the numerical dental model to simulate wearing of the orthodontic appliance on the patient's dental tissues;
   calculating orthodontic change after wearing of the orthodontic appliance on the patient's dental tissues, based on the mechanical parameters and geometrical parameters included in the numerical orthodontic appliance model and the numerical dental model respectively; and
   assessing the orthodontic effect of the numerical orthodontic appliance model based on the orthodontic change;
   wherein the orthodontic appliance is an invisible shell orthodontic appliance representing teeth arrangement at an expected orthodontic state, and the mechanical parameters in the numerical orthodontic appliance model are dependent on a material used to make the orthodontic appliance;
   wherein the mechanical parameters of the patient's dental tissues include elastic modulus of periodontal tissue;
   wherein the mechanical parameters of the patient's dental tissues include changes of elastic modulus of periodontal tissue with time and strain.

2. The method according to claim 1, wherein the step of assessing the orthodontic effect of the numerical orthodontic appliance model based on the orthodontic change comprises:
   comparing the orthodontic change with the expected orthodontic state corresponding to the orthodontic appliance; and
   rejecting the orthodontic appliance when a difference between the orthodontic change and the expected orthodontic state exceeds a predetermined tolerance; and
   accepting the orthodontic appliance when the difference between the orthodontic change and the expected orthodontic state does not exceed the predetermined tolerance.

3. The method according to claim 2, wherein the method further comprises:
   using the numerical orthodontic appliance model of the accepted orthodontic appliance to manufacture a physical orthodontic appliance.

4. The method according to claim 2, wherein the method further comprises:
   modifying the numerical orthodontic appliance model for the rejected orthodontic appliance according to the orthodontic change.

5. The method according to claim 1, wherein the patent's dental tissues includes the patent's maxillary dentition and its periodontal tissue, or includes the patient's mandibular dentition and its periodontal tissue.

6. The method according to claim 1, wherein the patent's dental tissues includes one or more teeth in the patient's maxillary dentition or mandibular dentition and their periodontal tissue.

7. The method according to claim 1, wherein the numerical orthodontic appliance model is obtained by simulating a manufacturing process of the orthodontic appliance.

8. The method according to claim 1, wherein the numerical orthodontic appliance model is obtained by scanning a physical orthodontic appliance.

9. The method according to claim 1, wherein the mechanical parameters of the orthodontic appliance include elastic modulus of material of the orthodontic appliance, or elastic modulus of material of the orthodontic appliance and its changes with time and strain.

10. The method according to claim 1, wherein the step of calculating orthodontic change after wearing of the orthodontic appliance on the patient's dental tissues comprises:
    calculating deformation of periodontal tissue in the patient's dental tissues as represented by the numerical dental model, until an orthodontic force provided by the numerical orthodontic appliance model and a resisting force generated by the deformation of the periodontal tissue being represented by the numerical dental model reach a mechanical equilibrium state; and
    using tooth movement in the patient's dental tissues being represented by the numerical dental model at the mechanically equilibrium state as the orthodontic change.

11. The method according to claim 10, wherein the mechanical parameters of the patient's dental tissues include elastic modulus of the periodontal tissue and its changes with time and strain, and the mechanical parameters of the orthodontic appliance include elastic modulus of material of the orthodontic appliance and its changes with time and strain; the mechanical equilibrium state is a dynamic mechanical equilibrium state that varies with time.

12. The method according to claim 1, wherein the method further comprises:
    displaying the digitalized dental model and the orthodontic change therein.

13. A method for numerically simulating orthodontic effect of an orthodontic appliance, comprising:
    providing a numerical dental model representing a patient's dental tissues, wherein the numerical dental model comprises mechanical parameters and geometrical parameters of the patient's dental tissues;
    providing a set of numerical orthodontic appliance models, wherein the set of numerical orthodontic appliance models comprises at least a first numerical orthodontic appliance model representing a first orthodontic appliance and a second numerical orthodontic appliance model representing a second orthodontic appliance;

wherein the first numerical orthodontic appliance model includes mechanical parameters and geometrical parameters of the first orthodontic appliance, and the second numerical orthodontic appliance model includes mechanical parameters and geometrical parameters of the second orthodontic appliance;

combining the first numerical orthodontic appliance model with the numerical dental model to simulate wearing of the first orthodontic appliance on the patient's dental tissues;

calculating orthodontic change after wearing of the first orthodontic appliance on the patient's dental tissues, based on the mechanical parameters and geometrical parameters included in the first numerical orthodontic appliance model and the numerical dental model respectively; and modifying the second numerical orthodontic appliance model based on the orthodontic change;

wherein the first orthodontic appliance is an invisible shell orthodontic appliance representing teeth arrangement at a first expected orthodontic state and the second orthodontic appliance is an invisible shell orthodontic appliance representing teeth arrangement at a second expected orthodontic state after the first expected orthodontic state, and the mechanical parameters in the first and second numerical orthodontic appliance model are dependent on a material used to make the first and second orthodontic appliance;

wherein the mechanical parameters of the patient's dental tissues include elastic modulus of periodontal tissue;

wherein the mechanical parameters of the patient's dental tissues include changes of elastic modulus of periodontal tissue with time and strain.

14. A method for numerically simulating orthodontic effect of an orthodontic appliance, comprising:

providing a numerical dental model representing a patient's dental tissues, wherein the numerical dental model comprises mechanical parameters of the patient's dental tissues;

providing a set of numerical orthodontic appliance models, wherein the set of numerical orthodontic appliance models comprises at least a first numerical orthodontic appliance model representing a first orthodontic appliance and a second numerical orthodontic appliance model representing a second orthodontic appliance;

wherein the first numerical orthodontic appliance model includes mechanical parameters and geometrical parameters of the first orthodontic appliance, and the second numerical orthodontic appliance model includes mechanical parameters and geometrical parameters of the second orthodontic appliance;

combining the first numerical orthodontic appliance model with the numerical dental model to simulate wearing of the first orthodontic appliance on the patient's dental tissues;

calculating first orthodontic change after wearing of the first orthodontic appliance on the patient's dental tissues, based on the mechanical parameters and geometrical parameters included in the first numerical orthodontic appliance model and the numerical dental model respectively;

combining the second numerical orthodontic appliance model with the numerical dental model including the first orthodontic change, so as to simulate wearing of the second orthodontic appliance on the patient's dental tissues after wearing the first orthodontic appliance;

calculating second orthodontic change after wearing of the first orthodontic appliance and the second orthodontic appliance on the patient's dental tissues, based on the mechanical parameters and geometrical parameters included in the second numerical orthodontic appliance model and the numerical dental model respectively;

assessing the orthodontic effect of the first and second numerical orthodontic appliance models based on the second orthodontic change;

wherein the first orthodontic appliance is an invisible shell orthodontic appliance representing teeth arrangement at a first expected orthodontic state and the second orthodontic appliance is an invisible shell orthodontic appliance representing teeth arrangement at a second expected orthodontic state after the first expected orthodontic state, and the mechanical parameters in the first and second numerical orthodontic appliance models are dependent on a material used to make the first and second orthodontic appliances;

wherein the mechanical parameters of the patient's dental tissues include elastic modulus of periodontal tissue;

wherein the mechanical parameters of the patient's dental tissues include changes of elastic modulus of periodontal tissue with time and strain.

15. The method according to claim 14, wherein the step of assessing the orthodontic effect of the first and second numerical orthodontic appliance models based on the second orthodontic change comprises:

comparing the second orthodontic change with a second expected orthodontic state corresponding to the second orthodontic appliance; and rejecting the first and/or second orthodontic appliances when difference between the second orthodontic change and the second expected orthodontic state exceeds a predetermined tolerance; and accepting the first and/or second orthodontic appliances when the difference between the second orthodontic change and the second expected orthodontic state does not exceed the predetermined tolerance.

* * * * *